US006178354B1

(12) United States Patent
Gibson

(10) Patent No.: US 6,178,354 B1
(45) Date of Patent: Jan. 23, 2001

(54) INTERNAL MECHANISM FOR DISPLACING A SLIDABLE ELECTRODE

(75) Inventor: Charles A. Gibson, Malden, MA (US)

(73) Assignee: C. R. Bard, Inc., Murray Hill, NJ (US)

( * ) Notice: Under 35 U.S.C. 154(b), the term of this patent shall be extended for 0 days.

(21) Appl. No.: 09/203,922

(22) Filed: Dec. 2, 1998

(51) Int. Cl.[7] .................................................. A61N 1/05
(52) U.S. Cl. .......................................................... 607/116
(58) Field of Search .................... 607/116, 119, 607/122

(56) References Cited

U.S. PATENT DOCUMENTS

| | | |
|---|---|---|
| 452,220 | 5/1891 | Gunning . |
| 1,963,636 | 6/1934 | Wappler . |
| 2,102,270 | 12/1937 | Hyams . |
| 2,888,017 | 5/1959 | Wallace . |
| 4,565,200 | 1/1986 | Cosman ............................... 128/642 |
| 4,664,120 | 5/1987 | Hess ...................................... 128/642 |
| 5,035,695 | 7/1991 | Weber, Jr. et al. ..................... 606/42 |
| 5,163,938 | 11/1992 | Kambara et al. ....................... 606/47 |
| 5,197,964 | 3/1993 | Parins ..................................... 606/48 |
| 5,290,286 | 3/1994 | Parins ..................................... 606/50 |
| 5,327,889 | 7/1994 | Imran ....................................... 128/6 |
| 5,366,476 | 11/1994 | Noda ...................................... 606/45 |
| 5,386,818 | 2/1995 | Schneebaum et al. .................. 128/4 |
| 5,431,696 | 7/1995 | Atlee, III ............................. 607/124 |
| 5,482,037 | 1/1996 | Borghi ................................. 128/642 |
| 5,487,385 | 1/1996 | Avitall ................................. 128/642 |
| 5,578,067 | 11/1996 | Ekwall et al. ........................ 607/122 |
| 5,611,777 | 3/1997 | Bowden et al. ........................ 604/95 |
| 5,651,785 | 7/1997 | Abela et al. ............................ 606/15 |
| 5,720,718 | 2/1998 | Rosen et al. ............................ 604/22 |
| 5,722,401 | 3/1998 | Pietroski et al. ..................... 128/642 |
| 5,752,915 | 5/1998 | Newbauer et al. .................... 600/373 |
| 5,788,692 | 8/1999 | Campbell et al. ...................... 606/33 |
| 5,803,083 | 9/1998 | Buck et al. ........................... 128/660 |
| 5,824,030 | 10/1998 | Yang et al. ........................... 607/122 |
| 5,885,278 | 3/1999 | Fleischmann ......................... 606/41 |

FOREIGN PATENT DOCUMENTS

| | | | |
|---|---|---|---|
| 0 609 182 A1 | 1/1994 | (EP) | ............................. A61B/5/042 |
| WO 94/24931 | 11/1994 | (WO) . | |
| WO 95/18575 | 7/1995 | (WO) . | |
| WO 97/42893 | 11/1997 | (WO) | ............................. A61B/17/39 |

*Primary Examiner*—Scott M. Getzow
(74) *Attorney, Agent, or Firm*—Darby & Darby

(57) ABSTRACT

A medical device is disclosed which includes a displaceable electrode slidably mounted over the device. An electrode displacement mechanism is connected to the electrode, and may be actuated to displace the electrode relative to the medical device. The medical device may be used for therapeutic, diagnostic, or other medical procedures.

21 Claims, 2 Drawing Sheets

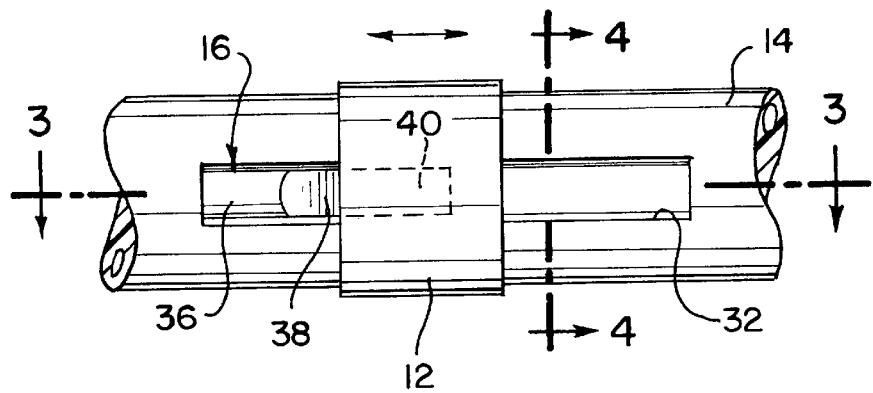
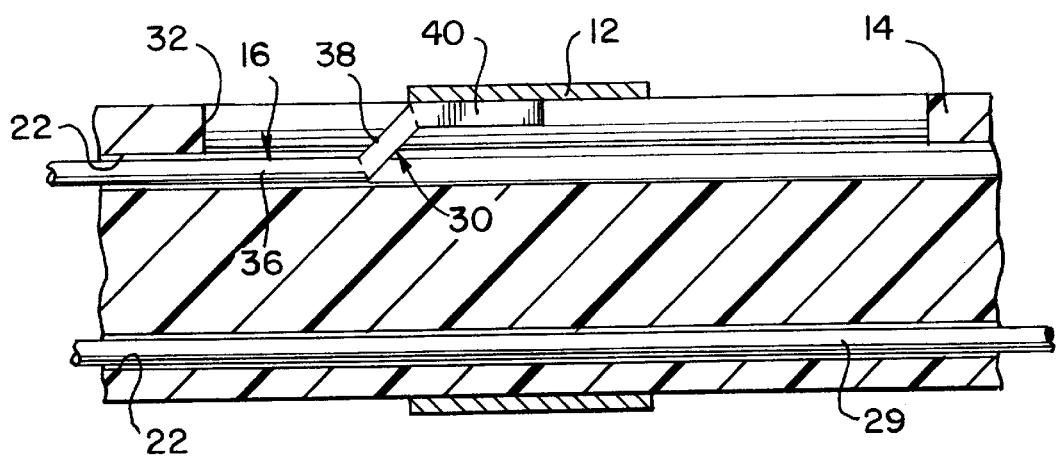
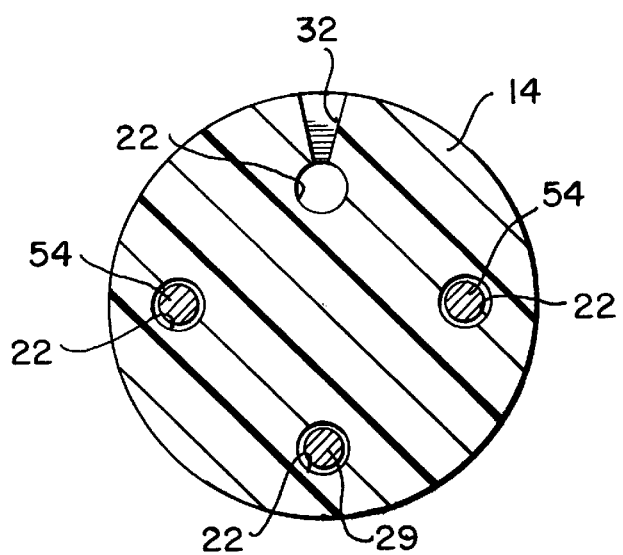

INTERNAL MECHANISM FOR DISPLACING A SLIDABLE ELECTRODE

FIELD OF THE INVENTION

This invention relates to medical devices for performing diagnostic, mapping, ablation, and other procedures and, more particularly, to a medical device including a displaceable electrode that is slidably mounted on the device and movable relative to the device.

BACKGROUND OF THE INVENTION

Cardiac arrhythmias, commonly known as irregular heart beats or racing hearts, are the result of various physical defects in the heart itself. One such defect is an extraneous strand of muscle fiber in the heart that provides an abnormal short-circuit pathway for electric impulses traveling through the heart tissue. This accessory pathway often causes the electric impulses that normally travel from the upper to the lower chamber of the heart to be fed back to the upper chamber, causing the heart to beat irregularly and therefore inefficiently pump blood.

Another common type of cardiac arrhythmia is ventricular tachycardia (VT), which may be a complication resulting from a heart attack or from a temporary reduction of blood supply to an area of heart muscle. VT often is caused by a tiny lesion, typically on the order of one to two millimeters, that is located close to the inner surface of the heart chamber. That lesion is often referred to as an "active site", because it does not fire in sequence with the rest of the heart muscle. VT causes the heart's normal rhythmic contraction to be altered, thereby affecting heart function. A typical symptom is rapid, inefficient heart beats.

Non-surgical procedures such as management with drugs are favored in the treatment of cardiac arrhythmias. However, some arrhythmias are not treatable with drugs. For example, drug therapy to combat VT is typically successful in only 30 to 50 percent of patients. Because of this low success rate, another conventional remedy is to perform a surgical procedure. According to these procedures, various incisions are made in the heart to block conduction pathways and thus divide the atrial area available for multiple wavelet reentry in an effort to abolish the arrhythmia. Alternatively, an automatic implantable cardioverter/defibrillator (AICD) can be surgically implanted into the patient, as described in U.S. Pat. No. 4,817,608 to Shapland et al. While these surgical procedures can be curative, they are associated with increased morbidity and mortality rates, and are extremely expensive. Even the use of an AICD requires major surgical intervention. Moreover, patients of advanced age or illness often cannot tolerate such invasive surgery.

Minimally invasive techniques have been developed which are used to locate cardiac regions responsible for the cardiac arrhythmia, and also to disable the short-circuit function of these areas. According to these techniques, electrical energy shocks are applied to a portion of the heart tissue to ablate that tissue and produce scars which interrupt the reentrant conduction pathways. The regions to be ablated are usually first determined by endocardial mapping techniques. Mapping typically involves the percutaneous introduction of a diagnostic catheter having one or more electrodes into the patient, passing the diagnostic catheter through a blood vessel (e.g. the femoral vein or aorta) and into an endocardial site (e.g., the atrium or ventricle of the heart), and inducing a tachycardia so that a continuous, simultaneous recording can be made with a multichannel recorder at each of several different endocardial positions. When a tachycardia focus is located, as indicated in the electrocardiogram recording, it is marked by means of a fluoroscopic image so that cardiac arrhythmias at the located site can be ablated. An ablation catheter with one or more electrodes can then provide electrical energy to the tissue adjacent the electrode to create a lesion in the tissue. One or more suitably positioned lesions will create a region of necrotic tissue to disable the malfunction caused by the tachycardia focus.

Conventional catheter ablation techniques have utilized catheters with a single electrode fitted at its tip as one electrical pole. The other electrical pole is conventionally provided by a backplate in contact with a patient's external body part to form a capacitive coupling of the ablation energy source (DC, laser, RF, etc.). Other ablation catheters are known in which multiple electrodes are provided.

Ablation is carried out by applying energy to the catheter electrodes once the electrodes are in contact with the cardiac tissue. The energy can be, for example, RF, DC, ultrasound, microwave, or laser radiation. When RF energy is delivered between the distal tip of a standard electrode catheter and a backplate, there is a localized RF heating effect. This creates a well-defined, discrete lesion slightly larger than the tip electrode (i.e., the "damage range" for the electrode), and also causes the temperature of the tissue in contact with the electrode to rise.

Often, to overcome cardiac arrhythmias such as atrial flutter and atrial fibrillation, it is necessary to create a long, continuous lesion (i.e., a linear lesion). One conventional ablation procedure for creating these linear lesions is commonly referred to as a "drag" method, in which an ablation catheter carrying one or more ablation electrodes is manipulated through a patient's blood vessels and to a desired location within the patient's heart. One or more of the electrodes is manipulated into contact with the heart tissue. Ablation energy is then delivered to the electrode(s), causing them to heat up and scar the adjacent tissue to create a lesion which is typically slightly larger than the surface area of the electrode contacting the tissue (the electrode's damage range). After the electrode has ablated the adjacent tissue, the clinician then manually moves the catheter a selected amount by pulling on the catheter shaft so that the electrode (s) are then aligned, and in contact, with different tissue, and ablation energy is again delivered to the electrode(s) to ablate that tissue. By continuing this procedure, the clinician attempts to create a continuous, linear lesion to block an aberrant pathway.

However, this method of dragging the catheter shaft has a number of disadvantages. For example, once the portion of the catheter shaft carrying the ablation electrode is making good tissue contact, it is undesirable to move the catheter shaft, because of the risk of losing the tissue contact.

Others have attempted to overcome this problem by using a relatively long, cylindrical electrode mounted over the catheter shaft. The long electrode can create longer lesions without requiring that the electrode (and thus the catheter shaft) be moved. However, using long electrodes also has significant drawbacks, one being that an elongated electrode detracts from the flexibility of the catheter, such that the catheter may not be able to assume a desired curve due to the straightening effects of the electrode(s).

Accordingly, it will be apparent that there continues to be a need for a device for performing ablations which facilitates the creation of linear lesions. In addition, there exists the need for a device which does not require the surgeon to physically drag the catheter shaft to create a linear lesion. The instant invention addresses these needs.

SUMMARY OF THE INVENTION

According to one aspect of the invention, an electrode is slidably mounted over a tubular member, such as a catheter shaft. An electrode displacement mechanism extends internally through the catheter shaft and engages the electrode through a longitudinal slot formed in the catheter side wall. The mechanism is operative to displace the electrode relative to the catheter shaft. In this manner, the catheter may be manipulated into place in contact with the tissue of the patient's heart, and the mechanism actuated to displace the electrode longitudinally relative to the catheter shaft and thus relative to the heart tissue. Thus, the electrode may be used to create linear lesions or may be moved for mapping and other diagnostic applications, with the mobility of the electrode allowing the clinician to dynamically adjust the spacing between the movable electrode and another fixed electrode mounted on the catheter shaft or elsewhere, all without the need for moving the catheter shaft itself.

While the invention has been described as having one slidable electrode, it will be apparent that the invention may comprise multiple slidable electrodes, which are driven by one or more electrode displacement mechanisms.

In one illustrative embodiment, the present invention is directed to a medical device comprising an elongated, tubular shaft having a longitudinal slot formed therein, an electrode slidably mounted on the shaft over the slot, and an electrode displacement mechanism extending through the shaft and slot to connect to the electrode, and operative to displace the electrode relative to the shaft.

In another illustrative embodiment, the invention is directed to a catheter for performing a medical procedure, comprising: an elongated, tubular shaft having a longitudinal slot formed at a predetermined location therein, the shaft defining at least one interior lumen therein, wherein the slot extends into the lumen; an electrode slidably mounted on the shaft in alignment with at least a portion of the slot; and an electrode displacement mechanism extending through the lumen and slot to connect to the electrode, the electrode displacement mechanism being operative to displace the electrode relative to the shaft.

DESCRIPTION OF THE DRAWINGS

Other objects, features and advantages of the invention discussed in the above summary of the invention will be more clearly understood from the following detailed description of preferred embodiments, which are illustrative only, when taken together with the accompanying drawings in which:

FIG. 2 is a fragmented side view, in enlarged scale, of the displaceable electrode included in the medical device of FIG. 1;

FIG. 3 is a cross-sectional view taken along the line 3—3 of FIG. 2 and looking in the direction of the arrows;

FIG. 4 is a cross-sectional view taken along the line 4—4 of FIG. 2 and looking in the direction of the arrows.

DETAILED DESCRIPTION OF THE PREFERRED EMBODIMENTS

Figure 1:
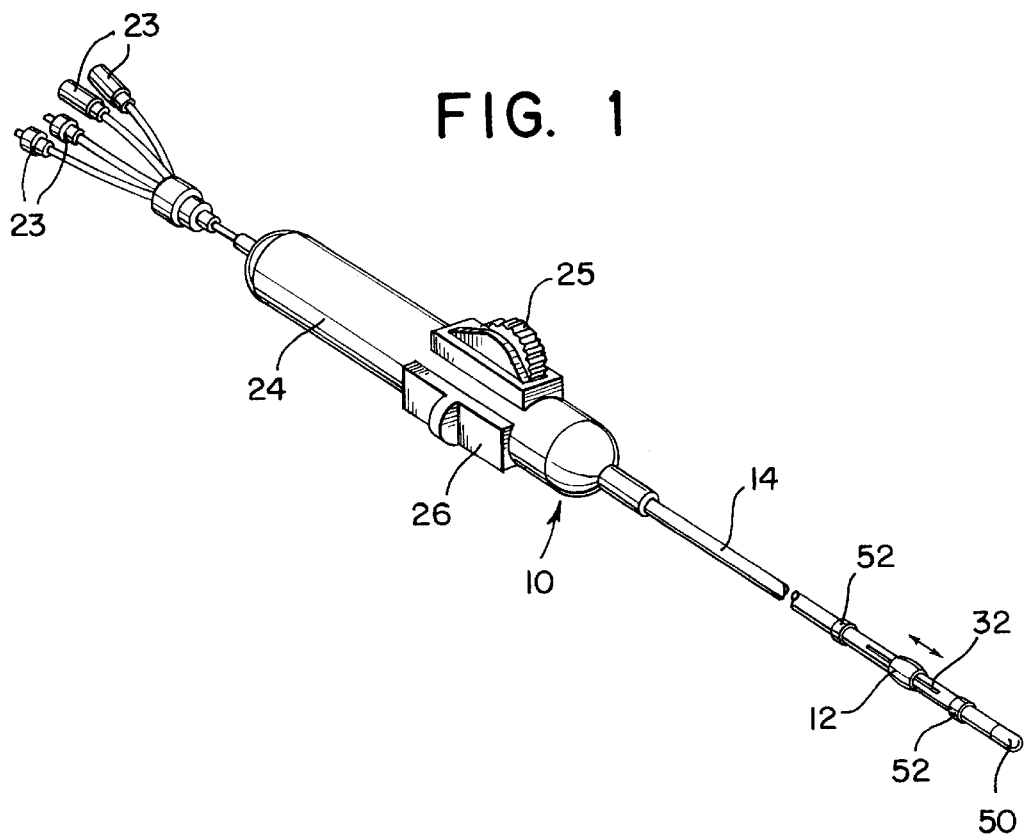
FIG. 1 is a perspective view of a medical device carrying a displaceable electrode illustrating one embodiment of the present invention.

Referring now to the drawings, and particularly to FIG. 1, there is shown a medical device 10 according to one illustrative embodiment of the present invention. In one illustrative embodiment, the medical device 10 has a displaceable electrode 12 which is slidably mounted over an elongated catheter shaft 14 of the device 10 and which is selectively movable relative to the catheter shaft in either a distal or proximal direction along the catheter shaft 14. An electrode displacement mechanism, generally designated 16, is connected to the displaceable electrode 12 and is operative to displace the electrode relative to the catheter shaft 14 and thus the medical device 10 as well. Thus, for example, in an ablation procedure, the device 10 may be manipulated through a patient's blood vessels until the electrode 12 is disposed in a desired location, such as in contact with an "active site" in the heart. Ablation energy is delivered to the electrode to destroy the adjacent tissue. The clinician then manipulates the electrode displacement mechanism 16 to move the electrode 12 relative to the shaft 14 a selected distance, and ablation energy is again delivered to the electrode to ablate the tissue. The procedure is repeated one or more times to create a continuous, linear lesion.

Referring to FIG. 1, the medical device 10 in one illustrative embodiment is in the form of a catheter, for example, an ablation catheter, mapping catheter, or other diagnostic catheter. It will be apparent that the medical device 10 of the present invention can take many different forms, such as any medical device having an insertion member to be inserted into a patient's body. In the illustrative embodiment, the catheter includes the catheter shaft 14, which is preferably a conventional, flexible shaft which can be manipulated through a patient's blood vessels and to a site of interest within the patient's body. The catheter shaft defines at least one interior lumen 22 (FIG. 3) which is sized to slidably receive a portion of the electrode displacement mechanism 16 therein. In a preferred embodiment, the catheter shaft defines a plurality of interior lumens 22 for passing various components through the respective lumens, as is described in greater detail below.

Figure 5:
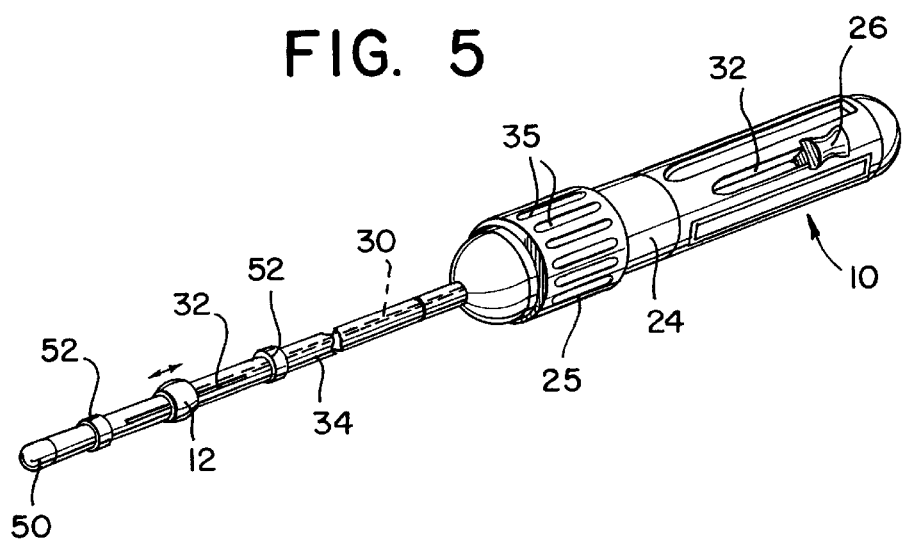
FIG. 5 is a perspective view of another illustrative embodiment of the medical device of the present invention.

In one embodiment, the catheter includes a control handle 24 for manipulating the electrode displacement mechanism 16 (FIG. 1). The catheter handle may take many different forms. One suitable form of control handle is shown in FIG. 1 and is disclosed in greater detail in U.S. Pat. No. 5,462,527 to Stevens-Wright, the disclosure of which is hereby expressly incorporated by reference as if fully set forth herein. Briefly, the control handle includes a slide actuator 26 which travels longitudinally along the control handle in a longitudinal slot (not shown) formed in the handle. Each end of the slot defines a stop limiting the extent of travel of the slide actuator. The slide actuator is connected to the electrode displacement mechanism 16 and therefore movement of the slide actuator translates into movement of the electrode displacement mechanism and thus the electrode 12, as is described in greater detail below. Another suitable form of control handle is disclosed in U.S. Pat. No. 5,611,777 to Bowden et al., which is shown in FIG. 5 and is expressly incorporated herein by reference.

The control handle 24 is connected to a plurality of connectors 23, which connect to suitable power supplies (not shown) to provide ablation energy to the slidable electrode 12, and to diagnostic equipment (not shown) to transmit sensing signals generated by the catheter electrodes, as is well known in the art and described in greater detail below.

The medical device 10 of the present invention is also preferably a steerable catheter, and thus the control handle also preferably includes a rotatable thumb wheel 25 rotatably mounted in the control handle 24, which can be rotated by a user to deflect the distal end of the catheter, as is well known to those skilled in the art, and as described in greater detail in U.S. Pat. No. 5,462,527, which has been incorporated herein by reference. As is well known to those skilled in the art, the thumb wheel is engaged to one or more pull wires 29 (FIG. 4) which extend through one or more of the lumens 22 in the catheter shaft 14 and are connected to the distal end of the catheter at an off-axis location, whereby tension applied to one or more of the pull wires causes the distal portion of the catheter to curve in a predetermined direction or directions. The thumb wheel may be knurled along its periphery or formed with upstanding ribs 35 to facilitate manipulation of the thumb wheel by a user's fingers.

In one illustrative embodiment, the electrode displacement mechanism 16 includes a relatively stiff displacing member 30 in the form of a mandrel which includes a first, proximal end securely connected to the slide actuator 26 inside the control handle 24. The mandrel may be in the form of a shaft, stiff wire, hypotube, or the like, and extends distally from the slide actuator through the handle 24, through one of the lumens 22, and then extends laterally with respect to the catheter shaft and into engagement with the inside surface of the slidable electrode 12.

The catheter shaft 14 preferably includes a longitudinal slot 32 formed at a predetermined location on the catheter shaft. The slot preferably extends into one of the lumens 22 to create an opening from the lumen to the outer surface of the catheter shaft 14. A portion of the mandrel 30 extends through the slot 32 for engagement with the inside surface of the slidable electrode 12 (FIG. 3). The slot may be formed with different dimensions to permit the electrode 12 to travel different distances along the catheter shaft 14. Preferably, the slot is between about one and about eight centimeters in length, but may, of course, be of any suitable length, subject to the dimensions of the control handle 24. The slot design may also serve to limit blood ingress into the lumen 22 which receives the mandrel 30. Specifically, as shown in FIG. 4, the slot 32 may be formed having a generally V-shaped cross-section to minimize the opening between the slot and lumen.

In one embodiment, the mandrel 30 includes an elongated, proximal segment 34 located inside the control handle 24, a tapered, cylindrical distal segment 36 extending through the catheter shaft 14, a transitioning segment 38 which extends distally and laterally outwardly through the catheter shaft 14, and a contact segment 40 which is sized for slidable receipt within the slot 32 and which may be connected to the inside surface of the displaceable electrode 12. The angled segment 38 extends into the longitudinal slot 32, and the contact segment 40 travels longitudinally within the slot. The distal segment 36 is preferably formed with a smaller cross-sectional diameter than the proximal segment 34 to maintain tip flexibility, while acting as a positive means for stopping overextended electrode movement.

The mandrel 30 may be formed of electrically conductive material, such that it serves not only to displace the movable electrode 12, but may also deliver electrical power to or from the electrode, in the case of either an ablation electrode or a sensing electrode. Alternatively, the mandrel may include an interior passageway through which one or more conductors extend to the electrode 12. In either case, the mandrel is preferably surrounded within a protective sheath which is treated with a hemo-compatible coating.

The mandrel 30 is preferably formed having a relatively high column strength to selectively displace the electrode 12 distally and proximally. Thus, when the mandrel is compressed by movement of the actuator 26 in a distal direction, the mandrel will resist bowing and will reliably advance the electrode 12 along the catheter shaft 14. In addition, in order to resist bowing, it is preferred to provide a lumen 22 sized to receive the mandrel 30 in a relatively tight manner while still allowing relative movement there between, such that the lumen walls assist in preventing the mandrel from bowing to any significant extent.

The slidable electrode 12 is preferably a conventional ring electrode having a suitably sized interior opening for slidable extension over the catheter shaft 14. In one embodiment, the catheter shaft may include a necked down segment in registration with the longitudinal slot 32. The electrode may be formed having a predetermined outer diameter so that it is flush with the outer diameter of the enlarged portion of the catheter shaft 14. Alternatively, the electrode 12 may be formed with an outer diameter larger than the outer diameter of the catheter shaft 14 so that it projects laterally outwardly from the catheter shaft 14 to provide a high-profiled electrode which facilitates tissue contact. In such an embodiment, the electrode 12 has a thickness sufficient to cause the outer contact surface thereof to project outwardly from the catheter shaft 14. As a result, the contact surface of the electrode generally contacts the patient's tissue before the catheter shaft 14 comes into contact with the tissue, even at locations where the tissue has an irregular surface.

While the slidable electrode 12 is preferably a ring electrode, it will be apparent that the electrode may take many different forms. For example, the electrode can be a strip electrode connected to the mandrel 30 and aligned with the slot 32. As used herein, "ring electrode" is defined as an electrode with a cylindrical inner surface for slidable extension over a tubular shaft such as catheter shaft 14. The outer surface of the ring electrode can take on any suitable configuration, depending on the particular use of the electrode.

Preferably, the medical device 10 includes a tip electrode 50 at the catheter distal end, which may be of conventional design, and one or more additional electrodes 52 at spaced apart locations along the catheter shaft. The electrode(s) may be used for monopolar ablation, bipolar ablation with the slidable electrode 12, mapping, and other functions well known to those skilled in the art. Typically, the electrodes 52 will be used for sensing, in either a monopolar or bipolar fashion, while the tip electrode 50 is typically used for making follow-up burns to fill in any gaps after the slidable electrode 12 has been used to create a linear lesion. However, other uses for the various electrodes are possible, as is well known to those skilled in the art. Each of the additional electrodes is mounted on the catheter shaft 14, and connected to a respective conductive wire 54 extending through one of the lumens 22 of the catheter. Also, each of the electrodes which is intended for use as an ablation electrode is preferably connected to a temperature sensor (not shown), which allows the clinician to monitor the temperature of the electrodes to avoid subjecting the tissue to excessive temperatures to avoid charring and coagulum. The temperature sensors can be thermocouples, thermistors, resistive thermal devices ("RTD"), or the like. Each temperature sensor has an associated conductive lead (not shown) which extends through one of the lumens 22 to a signal processor (not shown) for processing the electrical signals generated by the respective temperature sensors.

By locating the mandrel 30 inside the medical device 10, a number of benefits are realized. Firstly, the mandrel is kept out of contact with the patient's tissue. Thus, when the slidable electrode 12 is displaced relative to the patient's tissue, the mandrel does not rub against the patient's tissue and thus cannot get caught on that tissue. In addition, a stiff mandrel may be used, without increasing the diameter of the overall device 10.

In operation, a site of interest is determined by positioning the distal portion of the medical device 10 in the heart and sensing the electrical signals using one or more of the electrodes 12, 50, and 52, with the signals being transmitted to an appropriate diagnostic device via the connectors 23, or by using a different catheter with diagnostic capabilities. Once the site is located, one or more of the electrodes are moved to the proper location(s) and a power supply (not shown) is connected to one of the connectors 23 to energize one or more of the electrodes 12, 50, and 52 in either a constant voltage, power, or temperature mode as is well known to those skilled in the art. The electrodes can be energized simultaneously, sequentially, or in accordance with some other pattern. For example, the slidable electrode 12 can be energized and displaced relative to the shaft 14 to create a linear lesion, with the tip electrode 50 then being energized to perform any necessary follow-up burning as is well known in the art. Radio-frequency energy, typically in the range of about 250 Khz to 500 Khz, is delivered to the electrodes 12, 50, and 52 to ablate the patient's tissue. Energy flows from the respective electrodes 12, 50, and 52, through the tissue, to either one of the other electrodes (in a bipolar mode) or to a return plate (not shown), which is connected to the ground potential of the power supply, to complete the circuit. The flow of current through the circuit to the tissue causes heating which results in the destruction of the tissue near the electrodes 12, 50, and 52. If performed successfully, permanent interruption of the arrhythmia occurs and the patient is cured.

Often, in order to disrupt an arrhythmia, a long, continuous lesion must be formed. The medical device 10 of the present invention is designed to facilitate creating continuous lesions. The clinician simply manipulates the medical device 10 until the displaceable electrode 12 comes into contact with the patient's tissue and is located at one end of the arrhythmia. Ablation energy, for example, RF energy, is then delivered to the electrode 12, and the electrode is left in place for an amount of time sufficient to ablate the adjacent tissue. The clinician then manipulates the electrode displacement mechanism 16 so that the electrode travel a selected distance. In one embodiment, this is achieved by sliding the slide actuator 26 relative to the control handle 24. Once in the new location, ablation energy is again delivered to the electrode so that it ablates the adjacent tissue. This procedure is repeated one or more times to create the continuous lesion, without requiring the clinician to move the catheter shaft 14 or the entire medical device 10. Subsequently, the tip electrode 50 may be used for follow-up burning as described above.

From the foregoing, it will be apparent to those skilled in the art that the present invention provides a medical device which facilitates the creation of continuous lesions, without requiring an elongated electrode that hinders the flexibility of the medical device. In addition, the medical device of the present invention provides an easily actuated mechanism for displacing an electrode to facilitate creating continuous lesions.

Having thus described preferred embodiments of the present invention, it is to be understood that the above described arrangement and system is merely illustrative of the principles of the present invention, and that other arrangements and systems may be devised by those skilled in the art without departing from the spirit and scope of the invention as claimed below.

What is claimed is:

1. A medical device comprising:
   an elongated shaft having a longitudinal slot formed therein, the shaft defining at least one interior lumen therein, wherein the slot extends into the lumen and the lumen is formed with predetermined cross-sectional dimensions;
   at least one electrode slidably mounted on the shaft in alignment with at least a portion of the slot; and
   an electrode displacement mechanism comprising a displacing member formed with predetermined dimensions for extension through the lumen and the slot to connect to the electrode, the electrode displacement mechanism being operative to displace the displacing member relative to the shaft and thereby displace the electrode relative to the shaft.

2. The medical device of claim 1, wherein the displacing member comprises an elongated member extending through the lumen, an intermediate segment connected to the elongated member and extending through the slot, and a contact segment connected to the intermediate segment and to the electrode.

3. The medical device of claim 1, wherein the medical device further comprises a handle, and the electrode displacement mechanism comprises a slide actuator slidably mounted in the handle and connected to the displacing member.

4. The medical device of claim 1, wherein the slot is between about one and about eight centimeters long.

5. The medical device of claim 1, further including at least one additional electrode mounted on the catheter shaft at a fixed location.

6. The medical device of claim 1, wherein the electrode comprises a ring electrode.

7. The medical device of claim 1, wherein the medical device comprises a catheter.

8. The medical device of claim 7, wherein the catheter comprises a steerable catheter.

9. The medical device of claim 1, further including a plurality of electrodes slidably mounted on the shaft, and wherein the electrode displacement mechanism is connected to each of the electrodes and is operative to displace the electrodes relative to the shaft.

10. The medical device of claim 1, wherein the shaft defines a plurality of interior lumens.

11. A catheter for performing a medical procedure, the catheter comprising:
    an elongated, tubular shaft having a longitudinal slot formed at a predetermined location therein, the shaft defining at least one interior lumen therein, wherein the slot extends into the lumen;
    an electrode slidably mounted on the shaft in alignment with at least a portion of the slot; and
    an electrode displacement mechanism extending through the lumen and slot to connect to the electrode, the electrode displacement mechanism being operative to displace the electrode relative to the shaft.

12. The medical device of claim 11, wherein the electrode displacement mechanism comprises a mandrel extending through the lumen and the slot to connect to the electrode.

13. The medical device of claim 12, wherein the mandrel comprises an elongated member extending through the lumen, an intermediate segment connected to the elongated member and extending through the slot, and a contact segment connected to the intermediate segment and to the electrode.

14. The medical device of claim 11, wherein the medical device further comprises a handle, and the electrode displacement mechanism comprises a slide actuator slidably mounted in the handle.

15. The medical device of claim 11, wherein the slot is between about one and about eight centimeters long.

16. The medical device of claim 11, further including at least one additional electrode mounted on the catheter shaft at a fixed location.

17. The medical device of claim 11, wherein the electrode comprises a ring electrode.

18. The medical device of claim 11, wherein the medical device comprises a catheter.

19. The medical device of claim 18, wherein the catheter comprises a steerable catheter.

20. The medical device of claim 11, wherein the shaft defines a plurality of interior lumens.

21. The medical device of claim 11, further including a plurality of electrodes slidably mounted on the shaft, and wherein the electrode displacement mechanism is connected to each of the electrodes and is operative to displace the electrodes relative to the shaft.

* * * * *